US00PP10286P

United States Patent [19]

Zaiger et al.

[11] Patent Number: Plant 10,286

[45] Date of Patent: Mar. 17, 1998

[54] PEACH TREE "BRITTNEY LANE"

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 767,672

[22] Filed: Dec. 17, 1996

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new and distinct variety of peach tree (*Prunus persica*), its novelty consisting of the following unique combination of features that are desirable in a new variety:

1. Early maturity of the fruit.
2. Fruit with large size, good flavor and eating quality.
3. Fruit with an attractive red skin color.
4. Producing firm fruit with good handling and shipping quality.
5. Heavy and regular production of fruit.
6. Having a relatively low winter chilling requirement of approximately 350 hours.
7. Vigorous, upright tree growth.

1 Drawing Sheet

ORIGIN OF THE VARIETY

The new variety of peach tree was originated by us in our experimental orchard located near Modesto, Calif., as a first generation cross between two selected seedlings with field identification numbers 108ED650 and 74EC159. The material parent (108ED650) originated from the cross of a seedling selection (3GC117) with a seedling of unknown parentage. The seedling selection (3GC117) originated from a cross of two selected seedlings (29GA847 and 16GA1063). The selected seedling (29GA847) originated from a Red Grand Nectarine (U.S. Plant Pat. No. 1,060) crossed with Desert Gold Peach (non-patented). The seedling selection (16GA1063) originated from Sun Red Nectarine (non-patented) crossed with June Glo Nectarine (U.S. Plant Pat. No. 5,228). The paternal parent (74EC159) originated from a cross of an open pollinated May Grand Nectarine (U.S. Plant Pat. 2,794) seedling with a seedling originating from open pollinated Sam Houston Peach (non-patented) seed. A large group of seedlings from our first generation cross were grown and maintained under close observation, one early maturing seedling, which is the present variety, exhibited distinct and desirable fruit characteristics and was selected for asexual reproduction and commercialization.

Asexual Reproduction of the Variety

Asexual reproduction of the new and distinct variety of peach tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

The herein new and distinct variety of peach tree is of large size, vigorous, upright growth, and a regular and productive bearer of large size, yellow flesh, clingstone fruit with good flavor and eating quality. The fruit having firm flesh, good handling and shipping quality with a high degree of attractive red skin color. The tree is further characterized by having a relatively low winter chilling requirement of approximately 350 hours, producing early maturing fruit that are relatively uniform in size throughout the tree and in comparison to the low chilling Desert Gold Peach (non-patented) which ripens in the same maturity season, the new variety produces fruit that is larger in size, has firmer flesh, has greater handling and shipping quality and also a higher degree of attractive red skin color.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Pruned to vase shape.
- *Productivity.*—Productive.
- *Bearer.13* Regular.
- *Density.*—Medium dense.
- *Growth.*—Upright.

Trunk:
- *Size.*—Medium to large.
- *Texture.*—Medium shaggy.
- *Color.*—Brown to hair brown (5-D-6) to (5-E-4).

Branches:
- *Size.*—Medium.
- *Texture.*—Smooth to medium rough.
- *Lenticels.*—Medium number. Large size.
- *Color.*—Light brown to brown (5-C-5) to (5-D-4), varies with age of growth.

Leaves
- *Size.*—Large. Average length 6". Average width 1¾".

*Form.*—Lanceolate.
*Margin.*—Crenate.
*Thickness.*—Medium.
*Surface.*—Smooth.
*Petiole.*—Medium length. Medium thickness.
*Glands.*—Reinform. Medium size. Number varies from 1 to 4. Average number 2. Located on base of leaf blade and upper portion of petiole.
*Color.*—Upper surface — green to deep green (28-F-7) to (28-F-8). Lower surface — dull green to green (29-E-7) to (29-E-8).

Flower buds:
*Size.*—Medium to large.
*Length.*—Medium.
*Form.*—Plump.
*Pubescence.*—Pubescent.

Flowers:
*Size.*—Large, showy.
*Pollen.*—Present, self-fertile.
*Blooming period.*—Date of first bloom: Feb. 21, 1996. Date of full bloom: Feb. 26, 1996. Varies slightly with climatic conditions.
*Color.*—Pink.

Fruit:
*Maturity when described.*—Firm ripe.
*Date of first picking.*—Jun. 2, 1996.
*Date of last picking.*—Jun. 7, 1996.
*Size.*—Large. Average diameter axially 2½". Average transversely in suture plane 2¾".
*Form.*—Nearly globose, slightly flattened at base and apex.
*Suture.*—Shallow, extends from base to apex.
*Ventral surface.*—Nearly rounded, very slightly lipped.
*Apex.*—Usually slightly retuse, varies from slightly retuse to rounded.
*Base.*—Retuse.
*Cavity.*—Rounded to slightly elongated in suture plane. Average depth 7/16". Average breadth 15/16".

Flesh:
*Ripens.*—Evenly.
*Texture.*—Firm.
*Fibers.*—Few, fine, tender.
*Aroma.*—Moderate.
*Amygdalin.*—Undetected.
*Eating quality.*—Good.
*Flavor.*—Mild, good balance between acid and sugar.
*Color.*—Light yellow to yellow (3-A-4) to (3-A-6). Pit cavity, dull yellow to grayish yellow (3-B-4) to (3-B-5).

Skin:
*Thickness.*—Medium.
*Texture.*—Medium.
*Down.*—Moderate. Medium length.
*Tendency to crack.*—None.
*Color.*—Yellow to butter yellow ground color (4-A-4) to (4-A-5). Nearly overspread with red to madder red (9-A-7) to (9-B-7).

Stone:
*Type.*—Clingstone.
*Size.*—Large. Average length 1¼". Average width 1". Average thickness ½".
*Form.*—Obvoid.
*Base.*—Usually rounded, varies from rounded to straight.
*Apex.*—Slightly pointed, varies from slightly pointed to rounded.
*Surface.*—Irregularly furrowed toward apex, pitted toward base, pits vary from round to slightly elongated.
*Sides.*—Mostly equal, varies from equal to unequal.
*Tendency to split.*—Very slight.
*Color.*—Light brown to brown (5-D-4) to (5-E-4).

Use: Dessert. Market, local and long distance.
Keeping quality: Good.
Shipping quality: Good.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, which is of large size, vigorous, upright growth and a productive and regular bearer of large, yellow flesh clingstone fruit with good flavor and eating quality; the tree is further characterized by producing fruit with firm flesh, good handling and shipping quality, having a low winter chilling requirement of approximately 350 hours and in comparison to the Desert Gold Peach (non-patented), the new variety has firmer flesh, greater handling and shipping quality, and a higher degree of attractive red skin color.

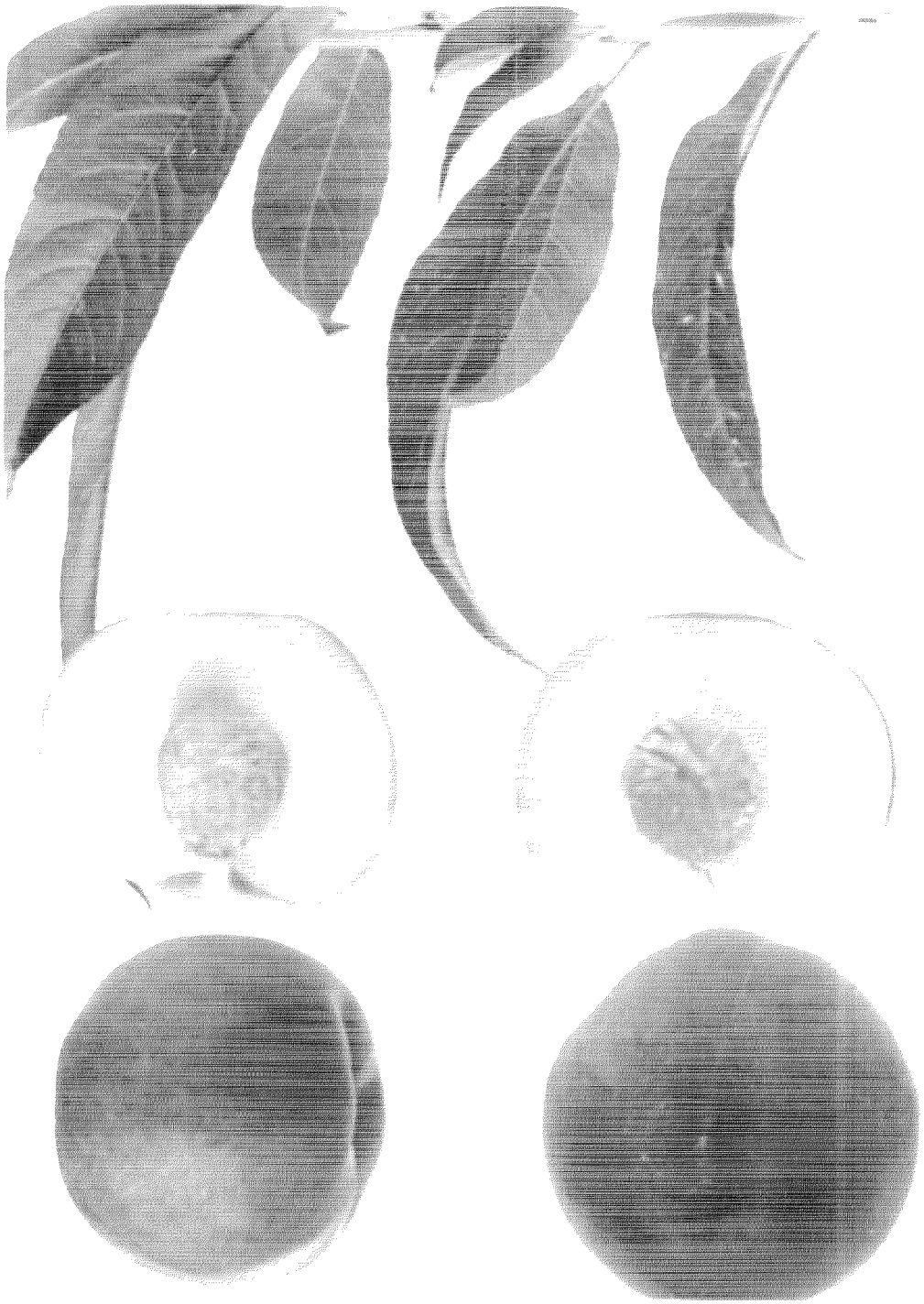

* * * * *